US010888255B2

(12) United States Patent
Nam et al.

(10) Patent No.: US 10,888,255 B2
(45) Date of Patent: Jan. 12, 2021

(54) BIOLOGICAL COMPONENT ESTIMATION APPARATUS AND OPERATION METHOD THEREOF

(71) Applicant: SAMSUNG ELECTRONICS CO., LTD., Suwon-si (KR)

(72) Inventors: Jung Yong Nam, Hwaseong-si (KR); Kun Sun Eom, Yongin-si (KR); Joon Hyung Lee, Seongnam-si (KR); Ki Young Chang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 197 days.

(21) Appl. No.: 15/892,111

(22) Filed: Feb. 8, 2018

(65) Prior Publication Data

US 2019/0090788 A1    Mar. 28, 2019

(30) Foreign Application Priority Data

Sep. 26, 2017  (KR) .................. 10-2017-0124226

(51) Int. Cl.
*A61B 5/1455* (2006.01)
*A61B 5/145* (2006.01)
*A61B 5/00* (2006.01)

(52) U.S. Cl.
CPC .......... *A61B 5/1455* (2013.01); *A61B 5/0059* (2013.01); *A61B 5/14532* (2013.01); *A61B 5/14546* (2013.01); *A61B 2562/043* (2013.01)

(58) Field of Classification Search
None
See application file for complete search history.

(56) References Cited

U.S. PATENT DOCUMENTS

| 5,351,686 A | 10/1994 | Steuer et al. |
| 5,372,136 A | 12/1994 | Steuer et al. |
| 5,456,253 A | 10/1995 | Steuer et al. |

(Continued)

FOREIGN PATENT DOCUMENTS

| JP | 2003-265440 A | 9/2003 |
| KR | 2003-0081369 A | 10/2003 |

(Continued)

OTHER PUBLICATIONS

Communication dated Oct. 24, 2018, issued by the European Patent Office in counterpart European Application No. 18175044.9.

*Primary Examiner* — Marjan Fardanesh
(74) *Attorney, Agent, or Firm* — Sughrue Mion, PLLC

(57) ABSTRACT

A biological component estimation apparatus according to an aspect of the present invention includes: a light detector array including a plurality of light detectors; a plurality of light sources disposed on both ends of the light detector array; and a processor configured to calculate a blood vessel alignment index, which indicates a degree of alignment of the biological component estimation apparatus with respect to blood vessels, by using an intensity of a first light that is measured by the plurality of light detectors after the first light is emitted to a user's skin from a first light source disposed on one end of the light detector array among the plurality of light sources, and an intensity of a second light that is measured by the plurality of light detectors after the second light is emitted to the user's skin from a second light source disposed on the other end of the light detector array among the plurality of light sources.

12 Claims, 10 Drawing Sheets

(56) References Cited

U.S. PATENT DOCUMENTS

| | | |
|---|---|---|
| 5,499,627 A | 3/1996 | Steuer et al. |
| 5,803,908 A | 9/1998 | Steuer et al. |
| 6,181,958 B1 | 1/2001 | Steuer et al. |
| 6,246,894 B1 | 6/2001 | Steuer et al. |
| 6,266,546 B1 | 7/2001 | Steuer et al. |
| 6,671,528 B2 | 12/2003 | Steuer et al. |
| 6,681,128 B2 | 1/2004 | Steuer et al. |
| 6,687,519 B2 | 2/2004 | Steuer et al. |
| 6,725,072 B2 | 4/2004 | Steuer et al. |
| 6,873,865 B2 | 3/2005 | Steuer et al. |
| 6,937,882 B2 | 8/2005 | Steuer et al. |
| 6,987,993 B2 | 1/2006 | Steuer et al. |
| 8,046,056 B2 | 10/2011 | Hwang et al. |
| 8,500,649 B2 | 8/2013 | Cho |
| 8,655,425 B2 | 2/2014 | Kim et al. |
| 2004/0116817 A1 | 6/2004 | Steuer et al. |
| 2006/0129037 A1 | 6/2006 | Kaufman et al. |
| 2007/0085995 A1 | 4/2007 | Pesach et al. |
| 2008/0081968 A1 | 4/2008 | Numada et al. |
| 2010/0036265 A1 | 2/2010 | Kim et al. |
| 2015/0157262 A1 | 6/2015 | Schuessler |
| 2015/0313516 A1 | 11/2015 | Shimizu et al. |
| 2017/0196455 A1 | 7/2017 | Mirov et al. |

FOREIGN PATENT DOCUMENTS

| | | |
|---|---|---|
| KR | 10-0829214 B1 | 5/2008 |
| KR | 10-0848118 B1 | 7/2008 |
| KR | 10-0866258 B1 | 11/2008 |
| KR | 10-1139401 B1 | 4/2012 |
| KR | 10-1146652 B1 | 5/2012 |
| KR | 10-1161537 B1 | 7/2012 |
| KR | 10-2012-0103860 A | 9/2012 |
| KR | 10-1432038 B1 | 9/2014 |
| KR | 10-1434847 B1 | 9/2014 |
| KR | 10-1571135 B1 | 12/2015 |
| KR | 10-2016-0144129 A | 12/2016 |

BIOLOGICAL COMPONENT ESTIMATION APPARATUS AND OPERATION METHOD THEREOF

CROSS-REFERENCE TO RELATED APPLICATION(S)

This application claims priority from Korean Patent Application No. 10-2017-0124226, filed on Sep. 26, 2017 in the Korean Intellectual Property Office, the disclosure of which is incorporated herein by reference in its entirety.

BACKGROUND

1. Field

Apparatuses and methods consistent with exemplary embodiments relate to estimating a biological component in a non-invasive manner, and more particularly to a biological component estimation apparatus, which calculates a blood vessel alignment index and determines a degree of alignment of blood vessels based on the calculation, and an operation method thereof.

2. Description of the Related Art

Blood components, particularly a triglyceride concentration, may be estimated by a measurement apparatus in a non-invasive manner. The measurement apparatus may include a light source and a light detector array, and may be placed at a blood vessel portion to receive a signal of light that is scattered after passing through blood. More particularly, a change in the blood component concentration indicates a change in a scattering coefficient of blood, such that the blood component concentration may be estimated by obtaining the change in the scattering coefficient of blood from the change in the signal of scattered light.

In the non-invasive method using optical technology, noise increases even when the position of a measurement apparatus slightly strays from a blood vessel portion. Such increase in noise reduces reliability of an optical measurement of blood components.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide a biological component estimation apparatus, which calculates a blood vessel alignment index and determines a degree of alignment of blood vessels based on the blood vessel alignment index, and an operation method thereof.

According to an aspect of an exemplary embodiment, there is provided a biological component estimation apparatus including: a light detector array including a plurality of light detectors; a plurality of light sources comprising a first light source disposed at a first end of the light detector array and a second light source disposed at a second end of the light detector array; and a processor configured to calculate a blood vessel alignment index, which indicates a degree of alignment of the biological component estimation apparatus with respect to blood vessels of a user, based on an intensity of a first light that is emitted from the first light source and measured by the light detector array when the first light is returned from the user, and an intensity of a second light that is emitted from the second light source to the user and measured by the light detector array when the second light is returned from the user.

The light detector array may be a linear array.

The processor may calculate: based on the measured intensity of the first light, an intensity slope of the first light which indicates a change in the measured intensity of the first light according to a distance between the first light source and each of the plurality of light detectors; based on the measured intensity of the second light, an intensity slope of the second light which indicates a change in the measured intensity of the second light according to a distance between the second light source and each of the plurality of light detectors; and the blood vessel alignment index by comparing the intensity slope of the first light with the intensity slope of the second light.

The processor may calculate, by using a regression analysis: the intensity slope of the first light based on the intensity of the first light that is measured by at least two first light detectors of the plurality of light detectors; and the intensity slope of the second light based on the intensity of the second light that is measured by at least two second light detectors of the plurality of light detectors corresponding to the at least two first light detectors.

A distance between the second light source and the at least two second light detectors may be equal to a distance between the first light source and the at least two first light detectors.

The processor may calculate: a ratio of the intensity of the first light, which is measured by two first light detectors of the plurality of light detectors, as the intensity slope of the first light; and a ratio of the intensity of the second light, which is measured by two second light detectors of the plurality of light detectors corresponding to the two first light detectors, as the intensity slope of the second light.

The processor may calculate, as the blood vessel alignment index, an absolute value of a difference between the intensity slope of the first light and the intensity slope of the second light.

The apparatus may further include a position adjuster configured to adjust positions of the light detector array and the plurality of light sources based on the calculated blood vessel alignment index.

The position adjuster may adjust the positions of the light detector array and the plurality of light sources so that the blood vessel alignment index is less than the predetermined value.

The processor may generate guide information that indicates a position of the biological component estimation apparatus that allows the blood vessel alignment index to be less than a predetermined value.

The apparatus may further include an output interface configured to output the generated guide information.

In response to the light detector array and the plurality of light sources being placed at a position where the blood vessel alignment index is less than a predetermined value, the processor may estimate a biological component of a user by using at least one of the light sources and at least one of the plurality of light detectors.

The biological component may include blood glucose, triglyceride, and cholesterol.

According to an aspect of another exemplary embodiment, there is provided an operation method of a biological component estimation apparatus, which includes a light detector array including a plurality of light detectors and a plurality of light sources including a first light source disposed at a first end of the light detector array and a second light source disposed at a second end of the light detector array, the method including: measuring an intensity of a first light which is emitted from the first light source to a user and reflected or scattered from the user; measuring an intensity of a second light which is emitted from the second light source to the user and is reflected or scattered from the user; and calculating a blood vessel alignment index, which indicates a degree of alignment of the biological component estimation apparatus with respect to blood vessels of the user, based on the measured intensity of the first light and the measured intensity of the second light.

The light detector array may be a linear array.

The calculating the blood vessel alignment index may include: based on the measured intensity of the first light, calculating an intensity slope of the first light which indicates a change in the measured intensity of the first light according to a distance between the first light source and each of the plurality of light detectors; based on the measured intensity of the second light, calculating an intensity slope of the second light which indicates a change in the measured intensity of the second light according to a distance between the second light source and each of the light detectors; and calculating the blood vessel alignment index by comparing the intensity slope of the first light with the intensity slope of the second light.

The calculating the intensity slope of the first light may include calculating, by using a regression analysis, the intensity slope of the first light by based on the intensity of the first light that is measured by at least two first light detectors of the plurality of light detectors; the calculating the intensity slope of the second light may include calculating, by using the regression analysis, the intensity slope of the second light based on the intensity of the second light that is measured by at least two second light detectors of the plurality of light detectors corresponding to the at least two light first detectors.

A distance between the second light source and the at least two second light detectors may be equal to a distance between the first light source and the at least two first light detectors.

The calculating the intensity slope of the first light may include calculating a ratio of the intensity of the first light, which is measured by two first light detectors of the plurality of light detectors, as the intensity slope of the first light; and the calculating the intensity slope of the second light may include calculating a ratio of the intensity of the second light, which is measured by two light second detectors of the plurality of light detectors corresponding to the two first light detectors, as the intensity slope of the second light.

The calculating the blood vessel alignment index may include calculating, as the blood vessel alignment index, an absolute value of a difference between the intensity slope of the first light and the intensity slope of the second light.

The method may include adjusting positions of the light detector array and the plurality of light sources based on the calculated blood vessel alignment index.

The adjusting the positions may include adjusting the positions of the light detector array and the plurality of light sources so that the blood vessel alignment index is less than a predetermined value.

The method may further include: generating guide information that indicates a position of the biological component estimation apparatus that allows the blood vessel alignment index to be less than a predetermined value; and outputting the generated guide information.

The method may further include, in response to the light detector array and the plurality of light sources being placed at a position where the blood vessel alignment index is less than a predetermined value, estimating a biological component of a user by using at least one of the light sources and at least one of the plurality of light detectors.

The biological component may include blood glucose, triglyceride, and cholesterol.

According to an aspect of another exemplary embodiment, there is provided a biosignal measuring device including: a light detector array comprising a plurality of light detectors that are arranged side-by-side in series; a first light source disposed at a first end of the light detector array; a second light source disposed at a second end of the light detector array, the second end opposing the first end in a longitudinal direction of the light detector array; and a processor configure to determine a degree of alignment of the biosignal measuring device with a blood vessel of a subject based on a comparison between an intensity of a first light that is emitted from the first light source and detected by the light detector array and an intensity of a second light that is emitted from the second light source and detected by the light detector array.

The processor may be further configure to determine the degree of alignment based on the comparison between the intensity of the first light that is emitted from the first light source and detected by at least two first light detectors of the light detector array and the intensity of a second light that is emitted from the second light source and detected by at least two second light detectors of the light detector array, wherein the at least two first light detectors may be closer to the first light source than any other light detectors among the plurality of light detectors included in the light detector array, and wherein the at least two second light detectors may be closer to the second light source than any other light detectors among the plurality of light detectors included in the light detector array.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
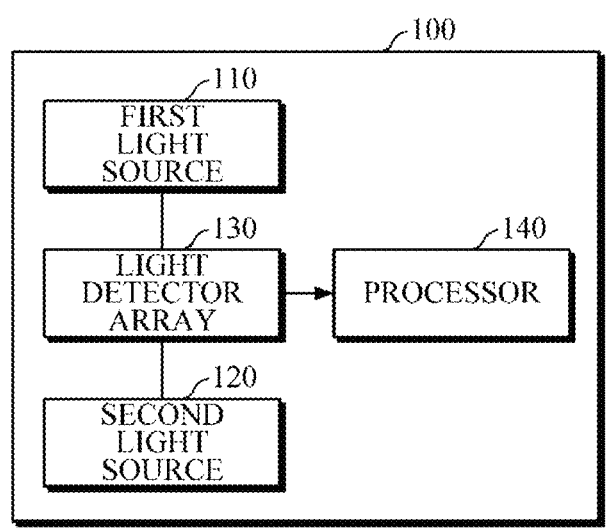
FIG. 1 is a block diagram illustrating an example of a biological component estimation apparatus.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

FIG. 1 is a block diagram illustrating an example of a biological component estimation apparatus. The biological component estimation apparatus 100 determines a degree of alignment of the biological component estimation apparatus 100 with respect to blood vessels. Based on the determination of the degree of alignment, the biological component estimation apparatus 100 generates and outputs guide information to accurately align the biological component estimation apparatus 100 with blood vessels, and estimates biological components. The biological component estimation apparatus 100 may be embedded in an electronic apparatus. Examples of the electronic apparatus may include a cellular phone, a smartphone, a tablet PC, a laptop computer, a personal digital assistant (PDA), a portable multimedia player (PMP), a navigation, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device is not limited to the above examples, and the wearable device is neither limited thereto.

Referring to FIG. 1, the biological component estimation apparatus 100 includes a first light source 110, a second light source 120, a light detector array 130, and a processor 140.

The first light source 110 and the second light source 120 may be disposed on both ends of the light detector array 130 to emit light to a user's skin. For example, the first light source 110 and the second light source 120 may emit near-infrared ray (NIR) or mid-infrared ray (MIR) to the user's skin. However, wavelengths of light emitted from each of the light sources 110 and 120 may vary depending on the purpose of measurement or the types of biological components to be measured. Further, each of the light sources 110 and 120 is not necessarily required to be configured as a single light emitting body, but may be configured as a group of a plurality of light emitting bodies. Each of the light sources 110 and 120 may include a light emitting diode (LED), a laser diode, a fluorescent body, or the like.

The light detector array 130 may include a plurality of light detectors. Each light detector receives light reflected or scattered from a user's skin, and measures an intensity of the received light. For example, the first light source 110, which is disposed at one end of the light detector array 130, emits a first light to a user's skin and measures an intensity of the first light that is reflected or scattered from the user's skin. The second light source 120, which is disposed at another end of the light detector array 130, emits a second light to the user's skin and measures an intensity of the second light that is reflected or scattered from the user's skin.

In the exemplary embodiment, the light detector array 130 may be a linear array, and each light detector may include a photo diode, a photo transistor (PTr), a charge-coupled device (CCD), or the like.

A user's skin, to which light is emitted, may be a portion of a wrist skin surface that is adjacent to the radial artery. The portion of the wrist skin surface, where the underlying radial artery passes, may be relatively little affected by external factors, such as a thickness of a skin tissue in the wrist, which cause an error in measurement. However, the portion is not limited thereto, and may be other distal portions of the human body, such as fingers, toes, or earlobes, which have a high density of blood vessels in the body.

The processor 140 may perform various operations including calculation of a blood vessel alignment index, alignment of the biological component estimation apparatus 100 with respect to blood vessels, and estimation of biological components, and the like. In particular, the blood vessel alignment index may indicate a degree of alignment of the biological component estimation apparatus 100 with respect to blood vessels.

According to a set period or a user's request, the processor 140 may control the first light source 110, the second light source 120, and the light detector array 130 to measure the intensity of the first light and the intensity of the second light.

The processor 140 calculates an intensity slope of the first light based on the measured intensity of the first light, and calculates an intensity slope of the second light based on the measured intensity of the second light. In this case, the intensity slope of the first light indicates a change in the measured intensity according to a distance between the first light source 110 and each light detector, and the intensity slope of the second light indicates a change in the measured intensity according to a distance between the second light source 120 and each light detector.

The measured intensity, which is measured by each light detector, becomes smaller as the distance between each light detector and the light sources 110 and 120 becomes larger. That is, the measured intensity of the first light, which is measured by each light detector after the first light is emitted from the first light source 110 and is reflected or scattered from a skin, becomes smaller as the distance between the first light source 110 and each light detector becomes larger; and the measured intensity of the second light, which is measured by each light detector after the second light is emitted from the second light source 120 and is reflected or scattered from a skin, becomes smaller as the distance between the second light source 120 and each light detector becomes larger. Accordingly, the change in the measured intensity of the first light according to the distance between the first light source 110 and each light detector may be defined as the intensity slope of the first light; and the change in the measured intensity of the second light according to the distance between the second light source 120 and each light detector may be defined as the intensity slope of the second light.

In the exemplary embodiment, the processor 140 may select at least two light detectors from among the plurality of light detectors, and may calculate the intensity slope of the first light based on the measured intensity of the first light that is measured by the selected at least two light detectors. The processor 140 may use a regression analysis to calculate the intensity slope of the first light. Further, the processor 140 may select at least two light detectors, which correspond to the at least two light detectors used to calculate the intensity slope of the first light, from among the plurality of light detectors, and may calculate the intensity slope of the second light by regression analysis using the measured intensity of the second light that is measured by the selected at least two light detectors. In particular, the distance between the first light source 110 and the at least two light detectors used to calculate the intensity slope of the first light may be equal to the distance between the second light source 120 and the at least two light detectors used to calculate the intensity slope of the second light. For example, the light detector array 130 may include ten light detectors #1 to #10 that are arranged side-by-side in series in the descending or ascending order of the numbers, the first light source 110 may be disposed on the side of the light detector #1, and the second light source 120 may be disposed on the side of the light detector #10. Based on the arrangement of the light detector array 130 and the light sources 110 and 120, the processor 140 may calculate the intensity slope of the first light using the intensity of the first light that is measured by the light detectors #1, #2, and #3, and may calculate the intensity slope of the second light using the intensity of the second light that is measured by the light detectors #10, #9, and #8. The light detectors #10, #9, and #8 may be arranged such that the distance from the second light source 120 to the light detectors #10, #9, and #8 is equal to the distance from the light detectors #1, #2, and #3 to the first light source 110, respectively.

The number and position of the light detectors, which are used to calculate the intensity slope of the first light, may vary depending on the performance and usage of a system; and the number and position of the light detectors, which are used to calculate the intensity slope of the second light, may be dependent on the number and position of the light detectors used to calculate the intensity slope of the first light.

In another example, the processor 140 may select two light detectors from among the plurality of light detectors, and may calculate, as the intensity slope of the first light, a ratio of the measured intensity of the first light that is measured by the selected two light detectors. Further, the processor 140 may select two light detectors, which correspond to the two light detectors used to calculate the intensity slope of the first light, from among the plurality of light detectors, and may calculate, as the intensity slope of the second light, a ratio of the measured intensity of the second light that is measured by the selected two light detectors. In this case, the distance between the first light source 110 and the two light detectors used to calculate the intensity slope of the first light may be equal to the distance between the second light source 120 and the two light detectors used to calculate the intensity slope of the second light. For example, the light detector array 130 may include ten light detectors #1 to #10 that are arranged in series in the descending or ascending order of the numbers, the first light source 110 may be disposed on the side of the light detector #1, and the second light source 120 may be disposed on the side of the light detector #10. Based on the arrangement of the light detector array 130 and the light sources 110 and 120, the processor 140 may calculate, as the intensity slope of the first light, a ratio of the measured intensity of the first light that is measured by the light detectors #1 and #5; and may calculate, as the intensity slope of the second light, a ratio of the measured intensity of the second light that is measured by the light detectors #10 and #6. The light detectors #1, #5, #6, and #10 may be arranged such that the distance from the second light source 120 to the light detectors #10 and #6 is equal to the distance from the first light source 110 to the light detectors #1 and #5, respectively.

The position of the light detectors, which are used to calculate the intensity slope of the first light, may be determined based on the performance and usage of a system. The position of the light detectors, which are used to calculate the intensity slope of the second light, may be determined based on the position of the light detectors used to calculate the intensity slope of the first light.

The processor 140 may calculate a blood vessel alignment index by comparing the intensity slope of the first light with the intensity slope of the second light. For example, the processor 140 may calculate, as the blood vessel alignment index, an absolute value of a difference between the intensity slope of the first light and the intensity slope of the second light.

The processor 140 may generate guide information based on the calculated blood vessel alignment index, to detect a position where the blood vessel alignment index is minimized, and may output the generated guide information through an internal or external output device of the biological component estimation apparatus 100. Here, the guide information may include information on a moving direction, a moving distance, and the like, of the biological component estimation apparatus 100, so that the first light source 110, the second light source 120, and the light detector array 130 may be accurately aligned with a blood vessel portion desired to be measured, that is, the blood vessel alignment index may be minimized.

Once the first light source 110, the second light source 120, and the light detector array 130 are placed at a position where the blood vessel alignment index is minimized, the processor 140 may estimate a biological component of a user by using all or some of the light sources 110 and 120, and all or some of the light detector array 130. Here, the biological component may be blood components, including blood glucose, cholesterol, triglyceride, and the like. In the exemplary embodiment, the processor 140 may measure a scattering coefficient of the user by using all or some of the light sources 110 and 120 and all or some of the light detector array 130, and may estimate a biological component of the user, such as blood glucose, cholesterol, triglyceride, and the like, by using the measured scattering coefficient.

Although FIG. 1 illustrates the biological component estimation apparatus 100 including two light sources 110 and 120, this is merely exemplary for convenience of explanation, and the biological component estimation apparatus 100 is not limited thereto. That is, the biological component estimation apparatus 100 may include three or more light sources disposed on both ends of the light detector array 130.

Figure 2:
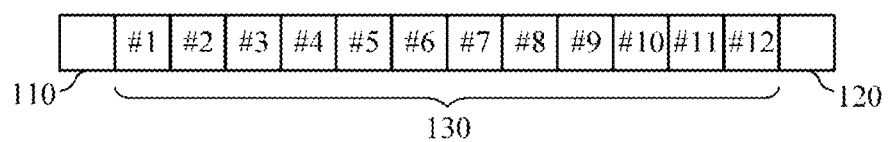
FIG. 2 is an exemplary diagram illustrating arrangement of light sources and a light detector array.

FIG. 2 is an exemplary diagram illustrating arrangement of light sources and a light detector array.

Referring to FIG. 2, the light detector array 130 may include a plurality of light detectors #1 to #12 and may be a linear array.

The first light source 110 may be disposed on one end of the light detector array 130 (e.g., one end on the side of the light detector #1), and the second light source 120 may be disposed on the other end of the light detector array 130 (e.g., one end on the side of the light detector #12).

Figure 3:
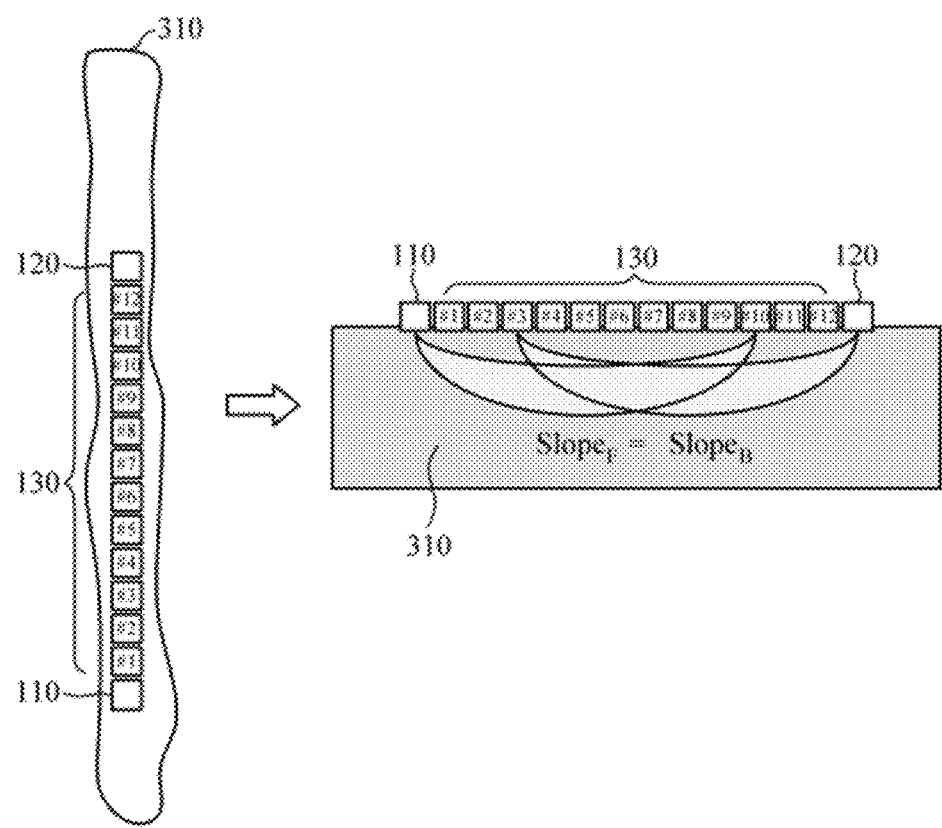
FIGS. 3 and 4 are diagrams explaining a principle of a method of aligning a biological component estimation apparatus with respect to blood vessels.
Figure 4:
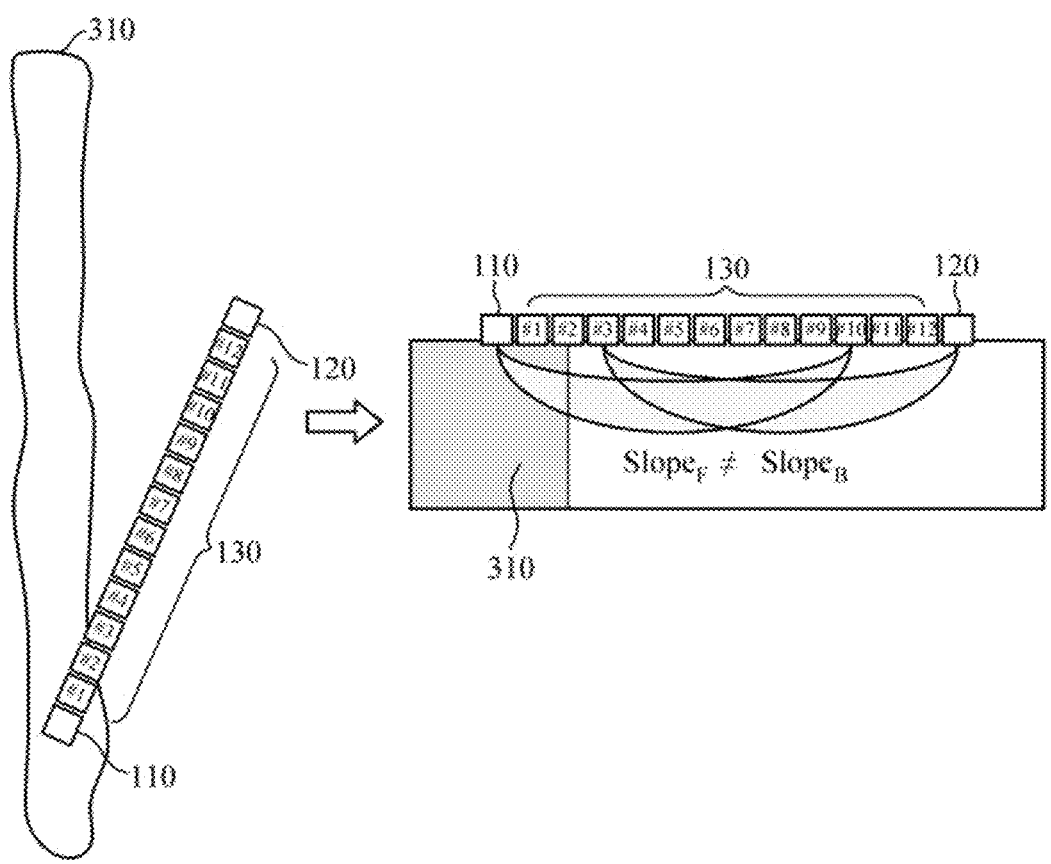

FIGS. 3 and 4 are diagrams explaining a principle of a method of aligning a biological component estimation apparatus with respect to blood vessels. More specifically, FIG. 3 is an exemplary diagram illustrating an example where the biological component estimation apparatus is aligned with a blood vessel portion; and FIG. 4 is an exemplary diagram illustrating an example where the biological component estimation apparatus is aligned on a portion other than the blood vessel portion.

Referring to FIGS. 1 and 3, in the case where the first light source 110, the second light source 120, and the light detector array 130 are aligned with a portion of blood vessels 310, both the first light and the second light pass through the blood vessels 310. Accordingly, the intensity slope of the first light and the intensity slope of the second light are the same or a difference therebetween is very small.

That is, in the case where the first light source 110, the second light source 120, and the light detector array 130 are aligned with the portion of blood vessels 310, the processor 140 calculates an intensity slope Slope F of the first light based on the intensity of the first light that is measured by the light detectors #1 to #10 after the first light is emitted from the first light source 110. Also, the processor 140 calculates an intensity slope Slope B of the second light based on the intensity of the second light that is measured by the light detectors #12 to #3, corresponding to the light detectors #1 to #10, after the second light is emitted from the second light source 120. In this case, the intensity slope Slope F of the first light and the intensity slope Slope B of the second light may be equal to each other or a difference therebetween is very small.

By contrast, referring to FIGS. 1 and 4, in the case where the first light source 110, the second light source 120, and the light detector array 130 are aligned with a portion other than the portion of the blood vessels 310, the first light passes through the blood vessels 310 but the second light does not pass the blood vessels 310. Accordingly, the intensity slope Slope F of the first light and the intensity slope Slope B of the second light are not the same, and a difference therebetween is large.

That is, in the case where the first light source 110, the second light source 120, and the light detector array 130 are aligned with a portion other than the portion of the blood vessels 310, the processor 140 calculates the intensity slope Slope F of the first light based on the intensity of the first light that is measured by the light detectors #1 to #10 after the first light is emitted from the first light source 110. In addition, the processor calculates the intensity slope Slope B of the second light based on the intensity of the second light that is measured by the light detectors #12 to #3, corresponding to light detectors #1 to #10, after the second light is emitted from the second light source 120. In this case, the intensity slope Slope F of the first light and the intensity slope Slope B of the second light are not the same, and a difference therebetween is large.

Accordingly, the difference between the intensity slope Slope F of the first light and the intensity slope Slope B of the second light indicates a degree of alignment of the biological component estimation apparatus 100 with respect to blood vessels. Thus, the processor 140 calculates, as a blood vessel alignment index, an absolute value of the difference between the intensity slope Slope F of the first light and the intensity slope Slope B of the second light. The processor 140 may align the biological component estimation apparatus 100 accurately with the portion of blood vessels by adjusting positions of the first light source 110, the second light source 120, and the light detector array 130 so that the blood vessel alignment index may be minimized.

While aligning the biological component estimation apparatus 100 accurately with the portion of blood vessels, the processor 140 may control all or some of the light sources 110 and 120 to emit light to a user's skin, and may control all or some of the light detector array 130 to detect light reflected or scattered from the user's skin, and use the detected light to estimate a biological component, thereby improving accuracy of estimation of the biological component.

Figure 5:
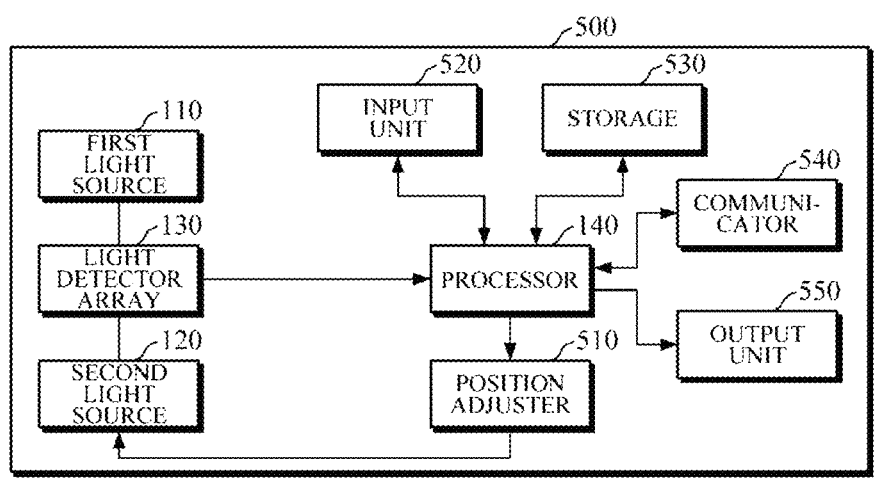
FIG. 5 is a block diagram illustrating another example of a biological component estimation apparatus.

FIG. 5 is a block diagram illustrating another example of a biological component estimation apparatus. The biological component estimation apparatus 500 determines a degree of alignment of the biological component estimation apparatus 100 with respect to blood vessels. Based on the determination of the degree of alignment, the biological component estimation apparatus 500 may align the biological component estimation apparatus 100 with blood vessels at a high accuracy, and may estimate biological components. The biological component estimation apparatus 500 may be embedded in an electronic apparatus. Examples of the electronic apparatus may include a cellular phone, a smartphone, a tablet PC, a laptop computer, a personal digital assistant (PDA), a portable multimedia player (PMP), a navigation, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device is not limited to the above examples, and the wearable device is neither limited thereto.

Referring to FIG. 5, the biological component estimation apparatus 500 includes a first light source 110, a second light source 120, a light detector array 130, a processor 140, a position adjuster 510, an input unit 520, a storage 530, a communicator (e.g., a communication interface) 540, and an output unit (e.g., an output interface) 550.

Here, the first light source 110, the second light source 120, the light detector array 130, and the processor 140 may be substantially the same as those described above with reference to FIGS. 1 to 4, such that detailed description thereof will be omitted.

The position adjuster 510 may automatically adjust positions of the first light source 110, the second light source 120, and the light detector array 130 based on the blood vessel alignment index calculated by the processor 140. In the exemplary embodiment, the position adjuster 510 may automatically adjust positions of the first light source 110, the second light source 120, and the light detector array 130, so that the blood vessel alignment index may be minimized. The position adjust 510 may include a motor to move the positions of the first light source 110, the second light source 120, and the light detector array 130. The processor 140 may determine that the blood vessel alignment index is minimized when the blood vessel alignment index is less than a reference index value that is stored in the storage 530.

The input unit 520 may receive input of various operation signals from a user. In the embodiment, the input unit 520 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 530 may store programs or commands for operation of the biological component estimation apparatus 500, and may store data input to and output from the biological component estimation apparatus 500. Further, the storage 530 may store data of the measured intensity of the first light and the measured intensity of the second light which are measured by the light detector array 130, data of the blood vessel alignment index calculated by the processor 140, the generated guide information, data of the estimated biological component, and various types of data used for estimation of biological components, and the like.

The storage 530 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the biological component estimation apparatus 500 may operate an external storage medium, such as web storage and the like, which performs a storage function of the storage 530 on the Internet.

The communicator 540 may communicate with an external device. For example, the communicator 540 may transmit, to the external device, data input from a user, data of the measured intensity of the first light and the measured intensity of the second light which are measured by the light detector array 130, data of the blood vessel alignment index calculated by the processor 140, the generated guide information, data of the estimated biological component, and various types of data used for estimation of biological components, and the like; or may receive various types of data, which are useful for estimation of biological components, from the external device.

In particular, the external device may be medical equipment using data input from a user, data of the measured intensity of the first light and the measured intensity of the second light which are measured by the light detector array 130, data of the blood vessel alignment index calculated by the processor 140, the generated guide information, data of the estimated biological component, and various types of data used for estimation of biological components, a printer to print out results, or a display device. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 540 may communicate with external devices by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra Wideband (UWB) communication, Ant+ communication, WIFI communication, Radio Frequency Identification (RFID) communication, 3G communication, 4G communication, 5G communication, and the like. However, this is merely exemplary and communication is not limited thereto.

The output unit 550 may output data input from a user, data of the measured intensity of the first light and the measured intensity of the second light which are measured by the light detector array 130, data of the blood vessel alignment index calculated by the processor 140, the generated guide information, data of the estimated biological component, and various types of data used for estimation of biological components, and the like. In the embodiment, the output unit 550 may output data input from a user, data of the measured intensity of the first light and the measured intensity of the second light which are measured by the light detector array 130, data of the blood vessel alignment index calculated by the processor 140, data of the estimated biological component, and various types of data used for estimation of biological components, the generated guide information, and the like, by using at least one of an acoustic method, a visual method, and a tactile method. To this end, the output unit 550 may include a display, a speaker, a vibrator, and the like.

Figure 6:
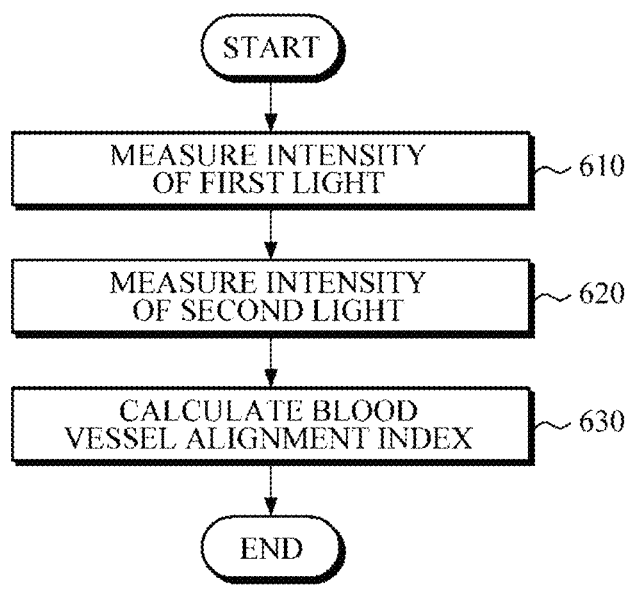
FIG. 6 is a block diagram illustrating an example of an operation method of a biological component estimation apparatus.

FIG. 6 is a block diagram illustrating an example of an operation method of a biological component estimation apparatus. The operation method of FIG. 6 may be performed by the biological component estimation apparatus 100.

As shown in FIGS. 1 and 6, the biological component estimation apparatus 100 may emit light to a user's skin by using the first light 110, and may measure an intensity of the first light reflected or scattered from the user's skin by using the light detector array 130 in operation 610.

The biological component estimation apparatus 100 may emit light to the user's skin by using the second light 120, and may measure an intensity of the second light reflected or scattered from the user's skin by using the light detector array 130 in operation 620.

Figure 7:
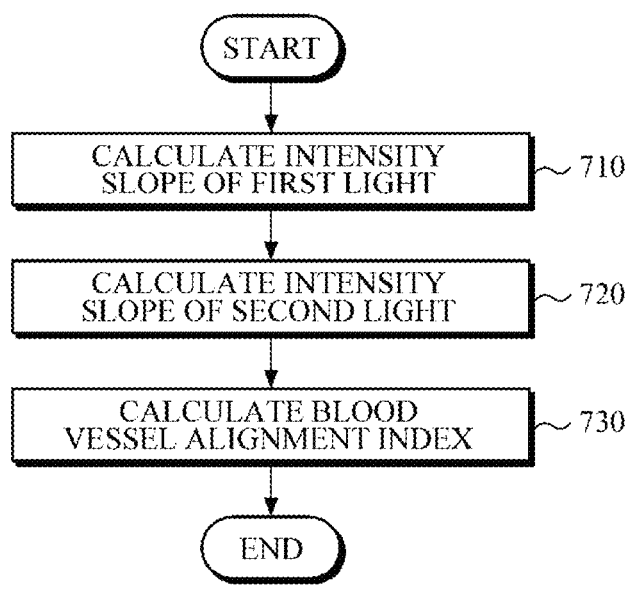
FIG. 7 is a flowchart illustrating an example of a method of calculating a blood vessel alignment index.

The biological component estimation apparatus 100 may calculate a blood vessel alignment index in operation 630, based on the measured intensity of the first light and the measured intensity of the second light. The blood vessel alignment index may indicate a degree of alignment of the biological component estimation apparatus 100 with respect to blood vessels FIG. 7 is a flowchart illustrating an example of a method of calculating a blood vessel alignment index. The method of calculating a blood vessel alignment index of FIG. 7 may be an example of calculating the blood vessel alignment index in operation 630 of FIG. 6.

As shown in FIGS. 1 and 7, the biological component estimation apparatus 100 may calculate the intensity slope of the first light based on the measured intensity of the first light in operation 710, and may calculate the intensity slope of the second light based on the measured intensity of the second light in operation 720. In this case, the intensity slope of the first light indicates a change in the measured intensity according to a distance between the first light source 110 and each light detector; and the intensity slope of the second light indicates a change in the measured intensity according to a distance between the second light source 120 and each light detector.

In the exemplary embodiment, the biological component estimation apparatus 100 may select at least two light detectors from among the plurality of light detectors, and may calculate the intensity slope of the first light by regression analysis using the measured intensity of the first light that is measured by the selected at least two light detectors. Further, the biological component estimation apparatus 100 may select at least two light detectors, which correspond to the at least two light detectors used to calculate the intensity slope of the first light, from among the plurality of light detectors, and may calculate the intensity slope of the second light by regression analysis using the measured intensity of the second light that is measured by the selected at least two light detectors. In this case, the distance between the first light source 110 and the at least two light detectors used to calculate the intensity slope of the first light may be equal to the distance between the second light source 120 and the at least two light detectors used to calculate the intensity slope of the second light.

In another example, the biological component estimation apparatus 100 may select two light detectors from among the plurality of light detectors, and may calculate, as the intensity slope of the first light, a ratio of the measured intensity of the first light that is measured by the selected two light detectors. Further, the biological component estimation apparatus 100 may select two light detectors, which correspond to the two light detectors used to calculate the intensity slope of the first light, from among the plurality of light detectors, and may calculate, as the intensity slope of the second light, a ratio of the measured intensity of the second light that is measured by the selected two light detectors. In this case, the distance between the first light source 110 and the two light detectors used to calculate the intensity slope of the first light may be equal to the distance between the second light source 120 and the two light detectors used to calculate the intensity slope of the second light.

The biological component estimation apparatus 100 may calculate a blood vessel alignment index by comparing the intensity slope of the first light with the intensity slope of the second light in operation 730. For example, the biological component estimation apparatus 100 may calculate, as the blood vessel alignment index, an absolute value of a difference between the intensity slope of the first light and the intensity slope of the second light.

Figure 8:
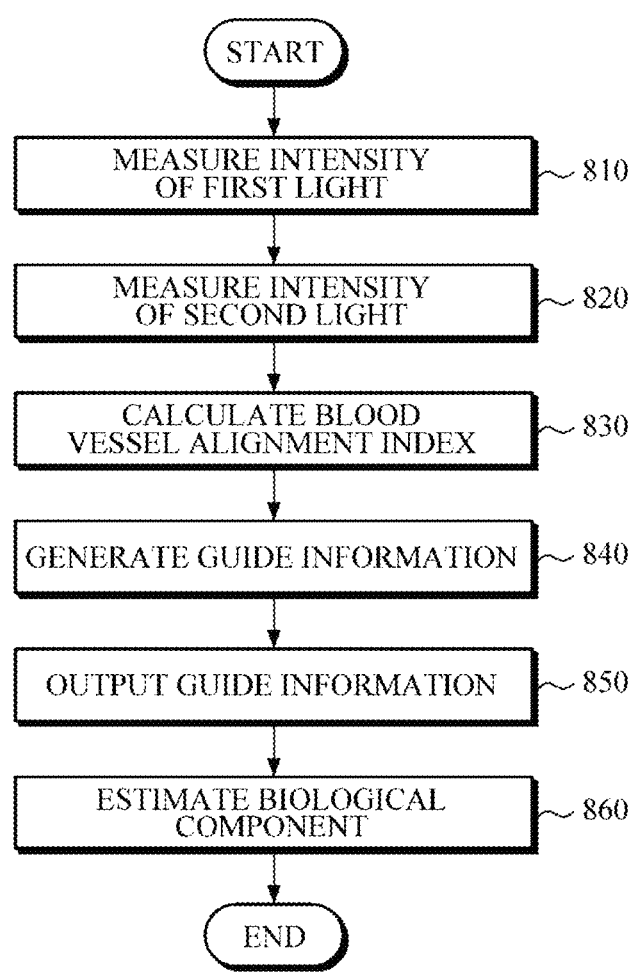
FIG. 8 is a block diagram illustrating another example of an operation method of a biological component estimation apparatus.

FIG. 8 is a block diagram illustrating another example of an operation method of a biological component estimation apparatus. The operation method of FIG. 8 may be performed by the biological component estimation apparatus 100 of FIG. 1.

Referring to FIGS. 1 and 8, the biological component estimation apparatus 100 may emit light to a user's skin by using the first light 110, and may measure an intensity of the first light reflected or scattered from the user's skin by using the light detector array 130 in operation 810.

The biological component estimation apparatus 100 may emit light to the user's skin by using the second light 120, and may measure an intensity of the second light reflected or scattered from the user's skin by using the light detector array 130 in operation 820.

The biological component estimation apparatus 100 may calculate a blood vessel alignment index in operation 830, which indicates a degree of alignment of the biological component estimation apparatus 100 with respect to blood vessels, based on the measured intensity of the first light and the measured intensity of the second light.

The biological component estimation apparatus 100 may generate guide information based on the calculated blood vessel alignment index to detect a position where the blood vessel alignment index is minimized in operation 840, and may output the generated guide information in operation 850. Here, the guide information may include information on a moving direction, a moving distance, and the like, of the biological component estimation apparatus 100, so that the first light source 110, the second light source 120, and the light detector array 130 may be accurately aligned with a blood vessel portion desired to be measured, that is, the blood vessel alignment index may be minimized.

Once the first light source 110, the second light source 120, and the light detector array 130 are placed at a position where the blood vessel alignment index is minimized, the biological component estimation apparatus 100 may estimate a biological component of a user by using all or some of the light sources 110 and 120, and all or some of the light detector array 130 in operation 860. Here, the biological component may be blood components, including blood glucose, cholesterol, triglyceride, and the like. For example, the biological component estimation apparatus 100 may measure a scattering coefficient of the user by using all or some of the light sources 110 and 120 and all or some of the light detector array 130, and may estimate a biological component of the user, such as blood glucose, cholesterol, triglyceride, and the like, by using the measured scattering coefficient.

Figure 9:
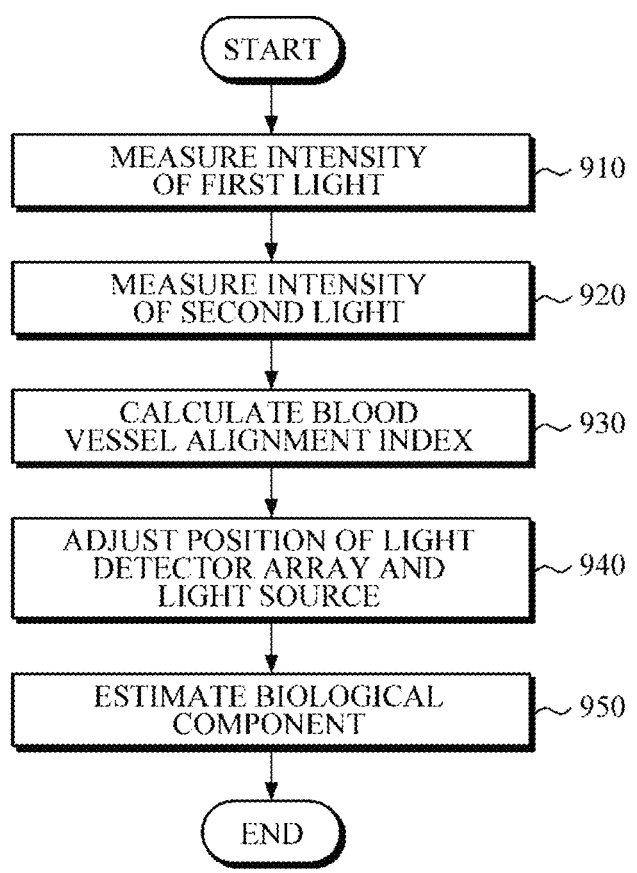
FIG. 9 is block diagram illustrating yet another example of an operation method of a biological component estimation apparatus.

FIG. 9 is block diagram illustrating yet another example of an operation method of a biological component estimation apparatus. The operation method of FIG. 9 may be performed by the biological component estimation apparatus 500 of FIG. 5.

Referring to FIGS. 5 and 9, the biological component estimation apparatus 500 may emit light to a user's skin by using the first light 110, and may measure an intensity of the first light reflected or scattered from the user's skin by using the light detector array 130 in operation 910.

The biological component estimation apparatus 500 may emit light to the user's skin by using the second light 120, and may measure an intensity of the second light reflected or scattered from the user's skin by using the light detector array 130 in operation 920.

The biological component estimation apparatus 500 may calculate a blood vessel alignment index in operation 930, which indicates a degree of alignment of the biological component estimation apparatus 500 with respect to blood vessels, based on the measured intensity of the first light and the measured intensity of the second light.

The biological component estimation apparatus 500 may automatically adjust positions of the first light source 110, the second light source 120, and the light detector array 130, so that the blood vessel alignment index may be minimized in operation 940.

Once the first light source 110, the second light source 120, and the light detector array 130 are placed at a position where the blood vessel alignment index is minimized, the biological component estimation apparatus 100 may estimate a biological component of a user by using all or some of the light sources 110 and 120, and all or some of the light detector array 130 in operation 950.

Figure 10:
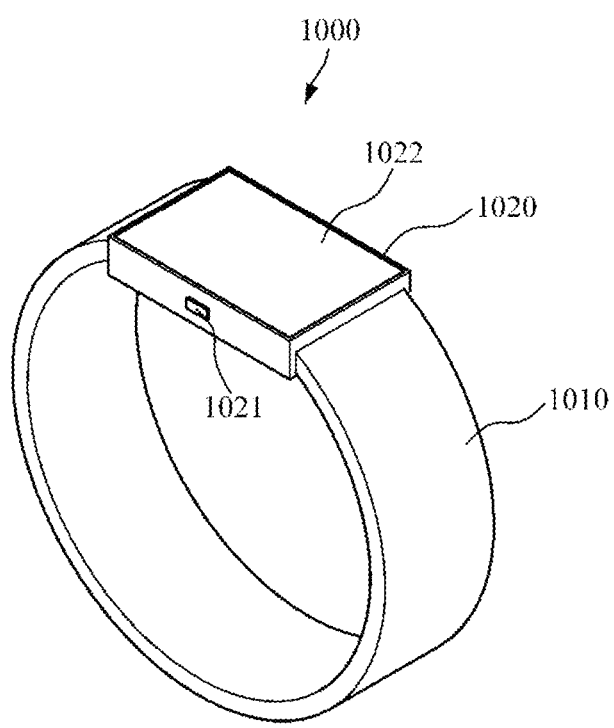
FIG. 10 is a perspective view of a wrist-type wearable device.

FIG. 10 is a perspective view of a wrist-type wearable device.

Referring to FIG. 10, the wrist-type wearable device 1000 includes a strap 1010 and a main body 1020.

The strap 1010 may be formed as a flexible band. However, this is merely exemplary and the strap 1010 is not limited thereto. That is, the strap 1010 may include various strap members configured to bend around a user's wrist.

The main body 1020 may include the aforementioned biological component estimation apparatuses 100 and 500. Further, the main body 1020 may include a battery which supplies power to the wrist-type wearable device 1000 and the biological component estimation apparatuses 100 and 500.

The wrist-type wearable device 1000 may further include an input unit 1021 and a display 1022 which are mounted at the main body 1020. The input unit 1021 may receive input of various operation signals from a user. The display 1022 may display data processed by the wrist-type wearable device 1000 and/or the biological component estimation apparatuses 100 and 500, processing result data, and the like.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A biological component estimation apparatus, comprising:
    a light detector array including a plurality of light detectors;
    a plurality of light sources comprising a first light source disposed at a first end of the light detector array and a second light source disposed at a second end of the light detector array; and
    a processor configured to calculate a blood vessel alignment index, which indicates a degree of alignment of the biological component estimation apparatus with respect to blood vessels of a user, based on an intensity of a first light that is emitted from the first light source and measured by the light detector array when the first light is returned from the user, and an intensity of a second light that is emitted from the second light source to the user and measured by the light detector array when the second light is returned from the user,
    wherein the processor calculates:
        based on the measured intensity of the first light, an intensity slope of the first light which indicates a change in the measured intensity of the first light according to a distance between the first light source and each of the plurality of light detectors;
        based on the measured intensity of the second light, an intensity slope of the second light which indicates a change in the measured intensity of the second light according to a distance between the second light source and each of the plurality of light detectors; and
        the blood vessel alignment index by comparing the intensity slope of the first light with the intensity slope of the second light.

2. The apparatus of claim 1, wherein the light detector array is a linear array.

3. The apparatus of claim 1, wherein the processor calculates, by using a regression analysis:
    the intensity slope of the first light based on the intensity of the first light that is measured by at least two first light detectors of the plurality of light detectors; and
    the intensity slope of the second light based on the intensity of the second light that is measured by at least two second light detectors of the plurality of light detectors corresponding to the at least two first light detectors.

4. The apparatus of claim 3, wherein a distance between the second light source and the at least two second light detectors is equal to a distance between the first light source and the at least two first light detectors.

5. The apparatus of claim 1, wherein the processor calculates:
    a ratio of the intensity of the first light, which is measured by two first light detectors of the plurality of light detectors, as the intensity slope of the first light; and
    a ratio of the intensity of the second light, which is measured by two second light detectors of the plurality of light detectors corresponding to the two first light detectors, as the intensity slope of the second light.

6. The apparatus of claim 1, wherein the processor calculates, as the blood vessel alignment index, an absolute value of a difference between the intensity slope of the first light and the intensity slope of the second light.

7. The apparatus of claim 1, further comprising a position adjuster configured to adjust positions of the light detector array and the plurality of light sources based on the calculated blood vessel alignment index.

8. The apparatus of claim 7, wherein the position adjuster adjusts the positions of the light detector array and the plurality of light sources so that the blood vessel alignment index is less than a predetermined value.

9. The apparatus of claim 1, wherein the processor generates guide information that indicates a position of the biological component estimation apparatus that allows the blood vessel alignment index to be less than a predetermined value.

10. The apparatus of claim 9, further comprising an output interface configured to output the generated guide information.

11. The apparatus of claim 1, wherein in response to the light detector array and the plurality of light sources being placed at a position where the blood vessel alignment index is less than a predetermined value, the processor estimates a biological component of the user by using at least one of the plurality of light sources and at least one of the plurality of light detectors.

12. The apparatus of claim 11, wherein the biological component comprises blood glucose, triglyceride, and cholesterol.

* * * * *